United States Patent
Bauss et al.

(10) Patent No.: US 10,512,725 B1
(45) Date of Patent: Dec. 24, 2019

(54) INFORMATION TRANSMITTER ATTACHED TO MEDICATION CONTAINER

(71) Applicant: SHL MEDICAL AG, Zug (CH)

(72) Inventors: Markus Bauss, Lengdorf (DE); Per Lindstedt, Värmdö (SE); Rasmus Renstad, Stockholm (SE); Nikolaj Hautaviita, Bro (SE); Daniel Säll, Segeltorp (SE)

(73) Assignee: SHL MEDICAL AG, Zug (CH)

( * ) Notice: Subject to any disclaimer, the term of this patent is extended or adjusted under 35 U.S.C. 154(b) by 0 days.

(21) Appl. No.: 16/428,385

(22) Filed: May 31, 2019

Related U.S. Application Data

(63) Continuation of application No. 15/514,719, filed as application No. PCT/EP2015/072704 on Oct. 1, 2015.

(Continued)

(30) Foreign Application Priority Data

Feb. 23, 2015 (EP) ..................... 15156116

(51) Int. Cl.
*G16H 20/17* (2018.01)
*A61M 5/20* (2006.01)
(Continued)

(52) U.S. Cl.
CPC ........ *A61M 5/2033* (2013.01); *A61M 5/3157* (2013.01); *A61M 15/00* (2013.01);
(Continued)

(58) Field of Classification Search
CPC .. A61M 5/2033; A61M 5/3157; A61M 15/00; A61M 2005/2013;
(Continued)

(56) References Cited

U.S. PATENT DOCUMENTS 7,304,578 B1 * 12/2007 Sayers ............... G06K 19/0716
340/572.1
8,355,753 B2   1/2013 Bochenko et al.
(Continued)

FOREIGN PATENT DOCUMENTS

EP         2243460       10/2010
TW      200504547 A      2/2005
(Continued)

OTHER PUBLICATIONS

International Search Report for Int. App. No. PCT/EP2015/072704, dated Feb. 12, 2016.

*Primary Examiner* — Nay Tun
(74) *Attorney, Agent, or Firm* — McDonnell Boehnen Hulbert & Berghoff LLP

(57) ABSTRACT

The present disclosure relates to an information transmitter having an electronics circuit, said electronics circuit has a transmitter; an antenna operably connected to said transmitter. Memory storage elements are also included having unique identification data with at least one activation element capable of activating said electronics circuit to transmit said unique identification data to external receivers. The present disclosure also relates to a medicament delivery device utilizing the information transmitter.

13 Claims, 9 Drawing Sheets

Related U.S. Application Data

(60) Provisional application No. 62/060,276, filed on Oct. 6, 2014.

(51) Int. Cl.
| | | |
|---|---|---|
| *A61M 5/315* | (2006.01) | |
| *G16H 40/63* | (2018.01) | |
| *G09B 5/06* | (2006.01) | |
| *G09B 1/32* | (2006.01) | |
| *G09B 1/14* | (2006.01) | |
| *G16H 20/13* | (2018.01) | |
| *G16H 20/10* | (2018.01) | |
| *A61M 15/00* | (2006.01) | |
| *G16H 10/20* | (2018.01) | |

(52) U.S. Cl.
CPC .............. *G09B 1/14* (2013.01); *G09B 1/325* (2013.01); *G09B 5/062* (2013.01); *G09B 5/065* (2013.01); *G16H 20/10* (2018.01); *G16H 20/13* (2018.01); *G16H 20/17* (2018.01); *G16H 40/63* (2018.01); *A61M 2005/202* (2013.01); *A61M 2005/2013* (2013.01); *A61M 2205/3569* (2013.01); *A61M 2205/3584* (2013.01); *A61M 2205/581* (2013.01); *A61M 2205/582* (2013.01); *A61M 2205/583* (2013.01); *A61M 2205/60* (2013.01); *A61M 2205/6009* (2013.01); *A61M 2205/609* (2013.01); *A61M 2205/6054* (2013.01); *G16H 10/20* (2018.01)

(58) Field of Classification Search
CPC .... A61M 2005/202; A61M 2205/3569; A61M 2205/3584; A61M 2205/581; A61M 2205/582; A61M 2205/583; A61M 2205/60; A61M 2205/6009; A61M 2205/6054; A61M 2205/609; G16H 40/63; G16H 10/20; G06F 19/3456; G06F 19/3462; G06F 19/3468; G09B 1/14; G09B 1/325; G09B 5/062; G09B 5/065

See application file for complete search history.

(56) References Cited

U.S. PATENT DOCUMENTS

| | | | |
|---|---|---|---|
| 2002/0188259 A1* | 12/2002 | Hickle | A61M 16/183 604/189 |
| 2004/0008123 A1* | 1/2004 | Carrender | G06K 19/07749 340/8.1 |
| 2004/0178112 A1 | 9/2004 | Snyder | |
| 2005/0241983 A1 | 11/2005 | Snyder et al. | |
| 2006/0169773 A1 | 8/2006 | Lyons et al. | |
| 2007/0129708 A1 | 6/2007 | Edwards et al. | |
| 2008/0054007 A1* | 3/2008 | Mador | A61J 7/0481 221/1 |
| 2008/0061153 A1* | 3/2008 | Hickle | A61M 16/183 235/492 |
| 2009/0043253 A1* | 2/2009 | Podaima | G16H 10/60 604/67 |
| 2010/0156642 A1* | 6/2010 | Lindsay | G06K 19/0716 340/572.7 |
| 2011/0111794 A1 | 5/2011 | Bochenko et al. | |
| 2011/0231204 A1 | 9/2011 | De La Huerga | |
| 2012/0024889 A1* | 2/2012 | Robertson | A61B 5/0002 222/23 |
| 2012/0289931 A1* | 11/2012 | Robinson | A61M 5/002 604/506 |
| 2012/0326885 A1 | 12/2012 | McCarty | |
| 2013/0046197 A1 | 2/2013 | Dlugos, Jr. et al. | |
| 2013/0181814 A1 | 7/2013 | Smith | |
| 2013/0184649 A1 | 7/2013 | Edwards et al. | |
| 2013/0285681 A1 | 10/2013 | Wilson et al. | |
| 2014/0292493 A1 | 10/2014 | Clarke et al. | |
| 2014/0312074 A1 | 10/2014 | Madsen et al. | |
| 2015/0025498 A1 | 1/2015 | Estes | |

FOREIGN PATENT DOCUMENTS

| | | |
|---|---|---|
| TW | 200706180 A | 2/2007 |
| TW | 201212888 A | 4/2012 |
| TW | 201406420 A | 2/2014 |
| WO | 2004/023245 | 3/2004 |
| WO | 2004/084116 | 9/2004 |
| WO | 2006/083933 A1 | 8/2006 |
| WO | 2012/108938 A1 | 8/2012 |
| WO | 2013/167701 | 11/2013 |

* cited by examiner

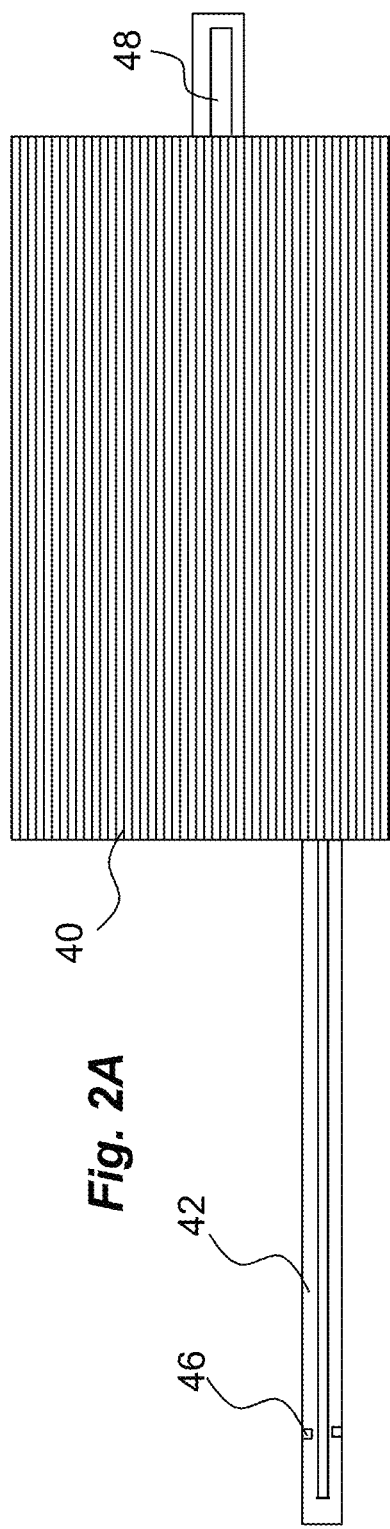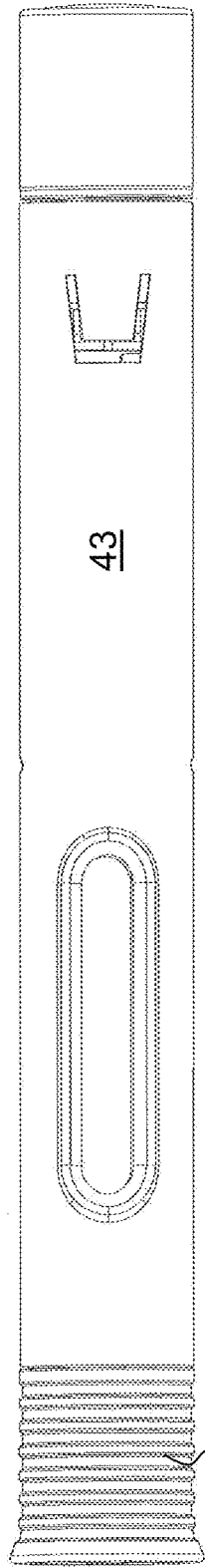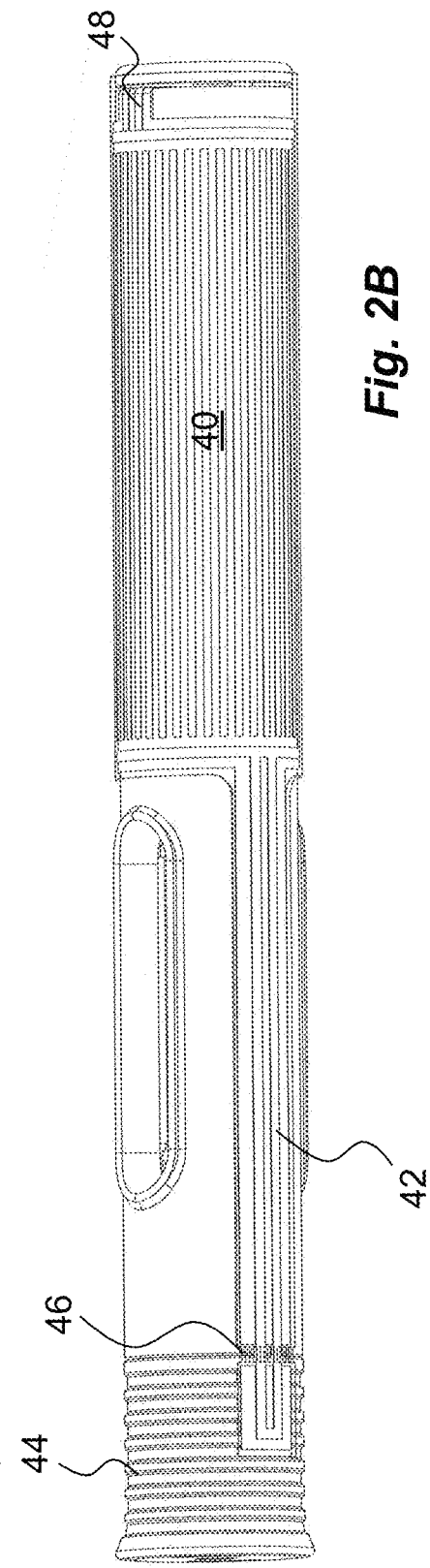
Fig. 2A
Fig. 2B

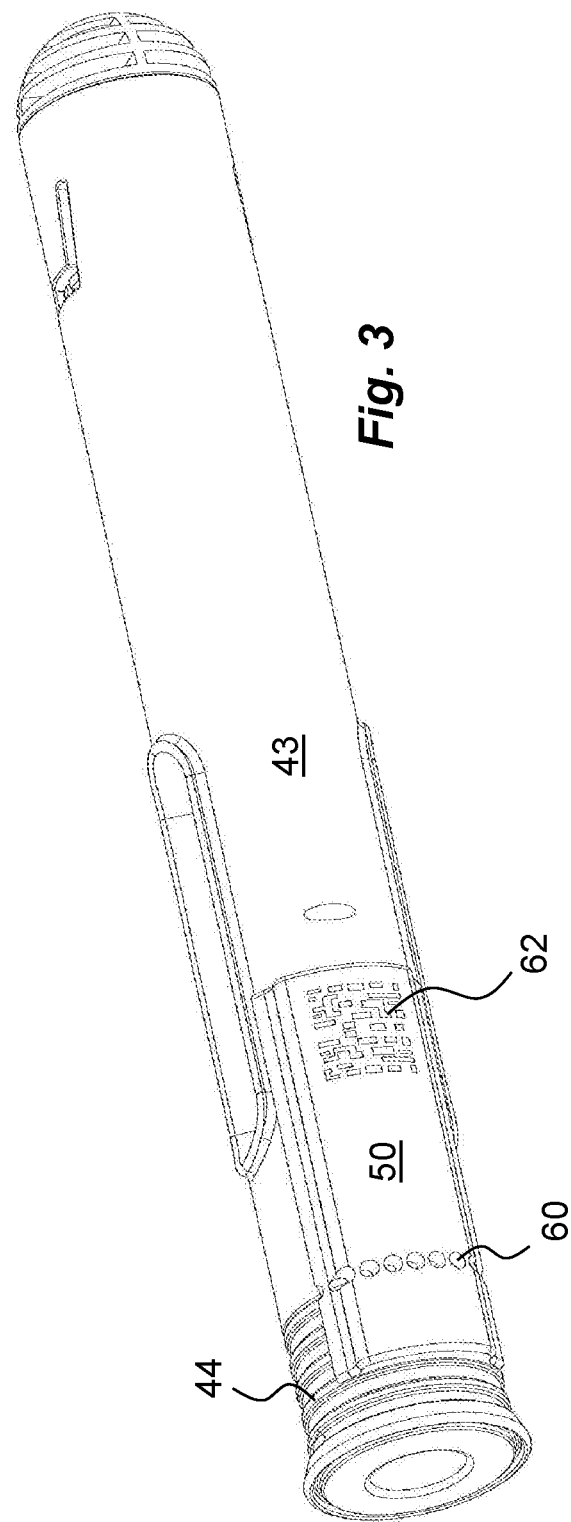

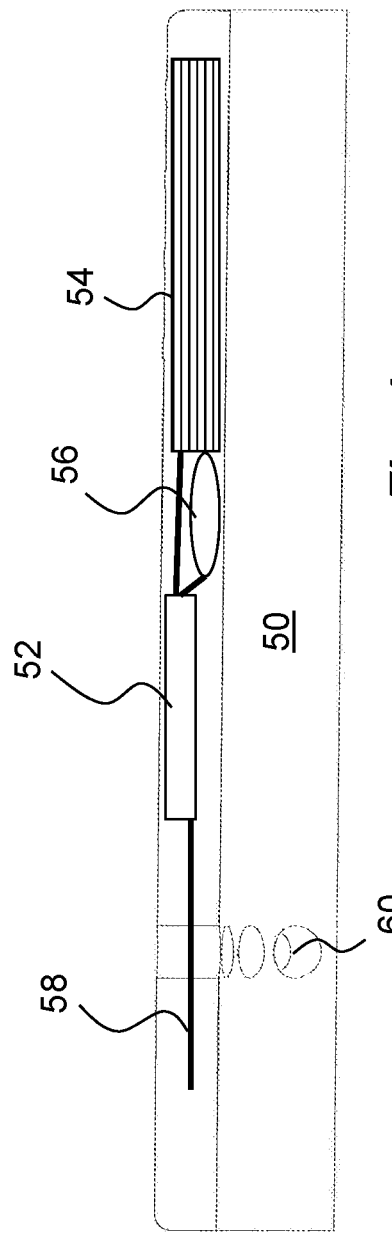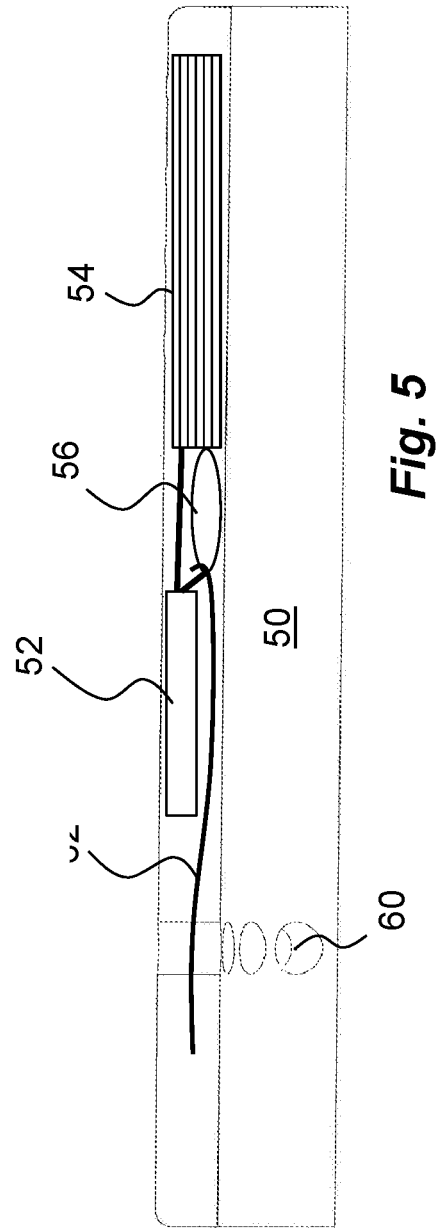

INFORMATION TRANSMITTER ATTACHED TO MEDICATION CONTAINER

CROSS REFERENCE TO RELATED APPLICATIONS

The present application is a Continuation of U.S. patent application Ser. No. 15/514,719, filed Mar. 27, 2017, which is a U.S. National Phase Application pursuant to 35 U.S.C. § 371 of International Application No. PCT/EP2015/072704 filed Oct. 1, 2015, which claims priority to U.S. Provisional Patent Application No. 62/060,276 filed Oct. 6, 2014 and European Patent Application No. 15156116.4, filed Feb. 23, 2015. The entire disclosure contents of these applications are herewith incorporated by reference into the present application.

TECHNICAL FIELD

The present invention relates to an information provider that is capable of transmitting unique identification information. The information provider is preferably arranged to a medicament delivery device and is further preferably arranged to communicate with smart devices.

BACKGROUND

Medicament delivery devices for self-administration have been on the market for a number of years. In order for the devices to be handled by non-professionals, they have to be easy to use and intuitive. Further, since many of the drugs are vital or at least very important to the patient there is a desire from physicians and other professionals to obtain information that the patients medicate according to prescribed schemes. The desired information could include the type of drug, delivery times and dates, dose size. Additional information that could be beneficial to the physician is that the drug has being taken using the correct procedure according to instructions for use; that the drug has the prescribed temperature during drug delivery; that the right injection depth has been used and that the correct injection speed has been used, when the medicament delivery device is an injector.

In order to obtain this information from the medicament delivery device, a number of solutions have been presented. Document WO 2004/084116 discloses a system for presenting and distributing medication information. According to the document, a medicament delivery device is arranged with communication mechanisms which will enable communication with a terminal device such as a cellular or a mobile phone or a PDA. A preferred communication standard is Bluetooth. The medicament delivery device is arranged with a number of sensors for monitoring and registering e.g. a dose delivery sequence. The idea is then to use the functionality of the terminal device, such as its display, its processor, its keyboard, etc. instead of providing the medicament delivery device with such features. The transfer of the functionality to the terminal device will reduce the cost of the medicament delivery device in comparison with medicament delivery devices provided with such functionality.

However, a drawback with the solution according to WO 2004/084116 is that a Bluetooth circuit, or the like wireless communication systems such as ANT or ZigBee, is built into the housing of the medicament delivery device. The communication system with its battery to power the circuit requires a certain space in a medicament delivery device. It is thus not so easy to modify existing designs or to easily provide existing designs with added functionality that communication systems can provide.

Other communication technologies that might be interesting are for instance radio frequency identification (RFID) tags. If passive RFID-tags are used, then no battery is required and the tags can be made very small. One favourable solution is to produce the tags as labels or stickers that can be attached to surfaces of a device. In the technical area of medicament delivery devices, RFID has been used to some extent for identifying certain components comprised in the medicament delivery device, completed operation sequence or for collecting information regarding adherence of a medicament delivery scheme.

Regarding identification, document U.S. Pat. No. 8,355,753 discloses a medication site arranged with a medication port to which a medicament container may be releasably attached. The neck portion of the medicament container is in one embodiment arranged with an RFID-tag with an antenna that can be connected or disconnected by a switch. When the medicament container is connected to the medication port, the switch connects the antenna and the information on the RFID-tag can be read by an RFID-reader in the medication site. The information contained in the RFID-tag may be the type of drug contained. According to another embodiment in U.S. Pat. No. 8,355,753, an RFID-tag may be arranged to be activated when medication has been delivered, thus sending information to the medication site that the delivery sequence is completed.

The drawback with the medication site according to U.S. Pat. No. 8,355,753 is that the device as such is rather complex and expensive, comprising a number of features and functions that are not a part of self-administering medicament delivery devices and certainly not for disposable medicament delivery devices.

SUMMARY

The aim of the present invention is to provide an information provider that may easily be used on a number of different devices and in particular medicament delivery devices for self-administration. Preferably the medicament delivery devices arranged with such information providers could be used with conventional smart devices common on the market and used by the majority of patients that handle medicament delivery devices for self-administration.

According to a main aspect of the invention, it comprises an information transmitter comprising an electronics circuit, said electronics circuit comprising a transmitter, an antenna operably connected to said transmitter, and memory storage elements comprising unique identification data. In order to activate and use the information transmitter, it is arranged with at least one activation element capable of activating said electronics circuit to transmit said unique identification data to external receivers.

Thus, the main idea is that the information transmitter is inactive before activation. Depending on the type of technology used, inactive may mean that the circuit is not switched on at all until it is activated. On the other hand it may mean that the circuit is in a standby or idle mode until activation. However, in a standby mode, the circuit may be programmed to "self-activate" at intervals to check certain conditions, and if these conditions are fulfilled, the circuit is activated.

According to a feasible solution, the at least one activation element may comprise an electrical circuit element that is affected upon activation and in that respect the electrical circuit element may be a loop that is broken upon activation. On the other hand the electrical circuit element may be a loop that is closed upon activation.

For some types of technologies, the information transmitter may further comprise an electrical power unit operably arranged to power said electronics circuit. The power unit may be a small battery or power cell, but may also be a photovoltaic panel or the like.

Instead of an electrical circuit element such as a loop, the at least one activation element may comprise a non-conductive member arranged between a lead of said power unit and said electronics circuit, which non-conductive member is removable upon activation. The non-conductive member may be a strip or the like that can be torn or pulled away so that the power unit is connected to the electronics circuit, activating it.

According to one favourable solution, the information transmitter is arranged in a flexible label attachable to a device. A label provides a number of advantages. It is easy to add functionality from the information transmitter to a device by attaching it to an exterior surface of the device. The information transmitter does thus not have to be built into the device. Further a label may be rather thin and does not add any substantial volume to a device when attached. An information transmitter as a label may further be arranged with additional information or indicia readable by a user, such as letters and numbers, or by scanning devices such as QR-codes or EAN-barcodes.

Further, the flexible label may be arranged with a tear line and that the electrical circuit element extends over said tear line. With such a solution the electronic circuit may be activated when a part of the label is torn away or otherwise removed by a user, which provides an intuitive activation operation.

A device that really may benefit from utilizing an information transmitter, and in particular in the form of a label is a medicament delivery device, especially for self-administration. A label containing the information transmitter may then be attached to an outer surface of the medicament delivery device. In that respect, the flexible label may be attached to said medicament delivery device such that the tear line is positioned between a housing part and a part that is detached prior to use. This may for instance be a protective cap that usually is removed before use. Again, it is an intuitive step to remove the protective cap, thereby tearing away a part of the label such that the electronics circuit of the information transmitter is activated. Here the activation could be performed by affecting a circuit element of the electronics circuit or it could be performed by pulling away the non-conductive strip of a power unit, thereby electrically connecting the power unit to the electronics circuit.

Regarding usable technologies, the electronics circuit may comprise Bluetooth technology, which has a few advantages. A Bluetooth transmitter may communicate with a smart device, which may not have to be at such a close range as e.g. NFC-technologies. Most smart devices nowadays are arranged with Bluetooth communication circuits, which this facilitates the transmission of information from the information transmitter to the smart device. A further advantage with Bluetooth is the possibility that an information transmitter of a medicament delivery device provided to a certain user is bonded to a smart device of said certain user. There is thus a tight connection between the medicament delivery devices that a user receives and is to use and his/hers personal smart devices. Thus, information from specific medicament delivery devices are only transmitted to specific smart devices.

These and other aspects of, and advantages with, the present invention will become apparent from the following detailed description of the invention and from the accompanying drawings.

BRIEF DESCRIPTION OF DRAWINGS

In the following detailed description of the invention, reference will be made to the accompanying drawings, of which FIG. 1 displays a first scenario according to the invention comprising an NFC-tag and a smart device, FIGS. 2A and 2B display the use of a label comprising an NFC-tag capable of providing status information of several features and functions of a medicament delivery device, FIG. 3 displays the use of a label comprising a Bluetooth-circuit capable of providing status information of a medicament delivery device, FIG. 4 displays a cross-sectional view of one alternative of the label of FIG. 3, FIG. 5 displays a cross-sectional view of a second alternative of the label of FIG. 3, FIG. 6 displays a second scenario according to the invention with a higher level of integration between NFC-tags and smart devices, FIGS. 7A and 7B display an example of the use of several NFC-tags in one medicament delivery device, FIG. 8 displays an example of physical integration of a medicament delivery device comprising NFC-tags and a smart device, and FIGS. 9 and 10 display the use of a packaging as a function provider.

DETAILED DESCRIPTION

Figure 1:
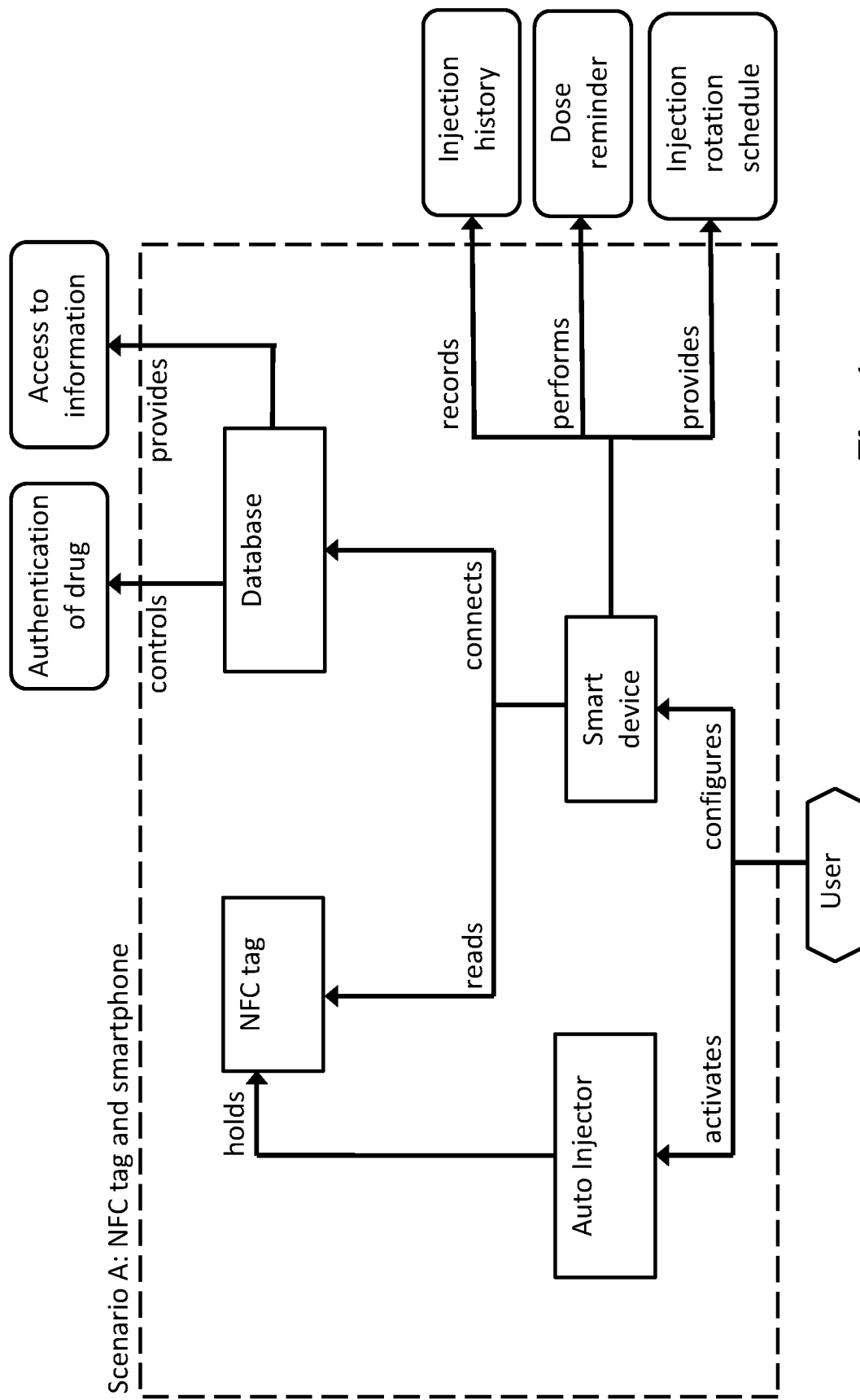

In the following description, the wording smart devices will be used. In this context, smart devices may include electronic devices that are provided with processors that are capable of running computer programs as well as storage space to store programs as well as data retrieved from different external sources. It is further to be understood that the smart devices are provided with communication systems that are capable of communicating with data networks in order to access different databases. It is to be understood that databases may be accessed via the internet, so called cloud services, and/or databases that are connected directly to and accessed via local area networks. It is further to be understood that the smart devices in this context comprise some sort of human-machine interface for two-way communication. The human-machine interface may comprise displays, keyboards, microphones, loudspeakers, I/O-ports for connection of peripherals. Further the smart devices may be provided with antennas for wireless communication with the networks. Also, the smart devices may be arranged with receiving and transmitting mechanisms capable of communicating with NFC tags as well as programs capable of establishing and handling the communication with the NFC tags.

Further, in the following description, the wording medicament delivery device will be used. In this context, medicament delivery devices may include a number of devices capable of delivering certain doses of medicament to a user, such as e.g. injection devices with or without injection needles, inhalers of all kinds, such as powder, aerosol driven, gas, nebulizers having mouth or nasal pieces, dispensers for medicament in tablet form. The medicament delivery devices may be of either disposable type or reusable type and may be provided with medicament containers suitably arranged for specific drugs in specific forms.

The communication system of the present application may comprise the use of radio frequency identification technology, RFID. In particular, high frequency RFID provides a number of advantages regarding communication. The possibilities of using HF RFID are numerous and in particular provides the use of Near Field Communication, NFC. NFC is particularly suitable because it is a set of standards for smartphones and the like smart devices to establish radio communication. NFC is a set of short-range wireless technologies, typically requiring a distance of 10 cm or less. NFC operates at 13.56 MHz on ISO/IEC 18000-3 air interface and at rates ranging from 106 kbit/s to 424 kbit/s. NFC always involves an initiator and a target; the initiator actively generates an RF field that can power a passive target. This enables NFC targets to take very simple form factors such as tags, stickers, key fobs, or cards that do not require batteries.

In the following description of the technology used the word NFC-tag will be used. In this context it is to be understood that NFC-tag will comprise an NFC-chip connected to a circuit as well as an antenna. NFC-tag is not limited to be integrated in a patch or label, but may be a stand-alone unit, or integrated in the material used for manufacturing medicament delivery devices. Further, the NFC-tag may include further features and components that are needed for the required or desired purposes and applications as will be apparent below.

NFC tags contain data and are typically read-only, but may be rewriteable. They can be custom-encoded by their manufacturers or use the specifications provided by the NFC Forum, an industry association charged with promoting the technology and setting key standards. The tags can securely store personal data such as debit and credit card information, loyalty program data, PINs and networking contacts, among other information.

Near-field communication uses magnetic induction between two loop antennas located within each other's near field, effectively forming an air-core transformer. There are two communication modes, passive and active mode. In the passive communication mode, the initiator device provides a carrier field and the target device answers by modulating the existing field. In this mode, the target device may draw its operating power from the initiator-provided electromagnetic field, thus making the target device a transponder. In the active communication mode, both initiator and target device communicate by alternately generating their own fields. A device deactivates its RF field while it is waiting for data. In this mode, both devices typically have power supplies. As to be understood in the following description in the area of medicament delivery devices, the initiator device is a smart device as defined above, and the target device is a medicament delivery device as defined above.

Regarding medicament delivery devices, they can be arranged with NFC tags in order to perform a number of tasks. The NFC tags may be arranged as labels on an outer or inner surface of a housing of a medicament delivery device. It may also be embedded or cast into the material of the medicament delivery device.

FIG. 1 displays a first possible scenario comprising NFC tags and smart devices. In its most simple application, the NFC tags may be arranged to perform functions that do not require specific approvals from national drug regulation authorities such as the FDA in USA that the device is e.g. safe and effective. Such functions may comprise authentication of the drug that is inside the medicament delivery device. In that respect, the NFC tags may be placed on the medicament containers, for example if the medicament delivery device is a reusable device that may be used for a number of medicament containers.

Alternatively the NFC tags may be a part of the medicament delivery device, either as a label added to the device during assembly or embedded into the material when casting the device, e.g. in the housing.

The NFC tags may further provide information regarding expiry date of the drug. Alternatively, the communication with the smart device may trigger the smart device to connect to a remote database where information regarding the drug may be retrieved, such as the expiry date. The information from the database may further include if any recalls can or have affected the unique drug and/or the medicament delivery device.

The NFC tags may further include functions that, when communicating with the smart device, may start programs or applications in the smart device that provides the user with information. The programs and/or applications may be stored in the smart device but may also, or instead, be stored in external databases that are either retrieved by the smart device or run via web browsers. In that respect, the NFC tags may trigger a web browser of the smart device to activate certain URL's. These may comprise e.g. instructions for use of the medicament delivery device, where the URL may lead to a web page containing a written description of how to use the device.

In addition, or instead, the targeted web page may include a video recording, that also could include a narrator, showing and describing how to use the device. Further information that could be provided to the user is contact information to health care providers, such as e.g. telephone numbers, e-mail addresses, maps etc. Further information to a user may comprise reminders and schedules for dose delivery, such as dose delivery intervals, at what times during the day the dose should be taken etc. This dose delivery information may be manually generated in that the user or a physician enters the information into the smart device, which could be done via a calendar function. The information could also be generated electronically from prescription, wherein the information is obtained through communication with external databases via networks. The smart device could then provide the user with reminding information when it is time to take a dose of medicament, wherein the reminder could include all sorts indications such as text messages on the display of the smart device, audible signals or voice messages, vibrations, flashes, just to mention a few possibilities.

Other types of information could comprise reminders and schedules regarding using different dose delivery sites, which may be quite important when injection devices are used and wherein repeated injections on the same site may cause scars tissue, and or where the drug injected may cause irritation of the skin. These schedules could comprise visual information on the display of the smart device showing graphically where on the body the next dose should be delivered. This type of information may then be displayed in connection with the reminder of taking a dose of medicament.

The storage facilities of the smart device may further be used to store unique ID of the drug used, wherein specific information may be connected to the drug in order to build up medicament delivery history. In this respect, medicament delivery history, e.g. injection history, may comprise information regarding date and time of information read by the smart device of performed drug delivery occasions. It is in this scenario thus important that the reading of the NFC-chip is performed close after the dose has been delivered in order for the information to be as accurate as possible.

The information may further, or instead, comprise delivered dose size, if for example the medicament delivery device may be provided with mechanism for setting and delivering different dose sizes. The information may be compared by the smart device with prescribed drug delivery intervals and/or dose sizes in order to detect any deviations. Any deviations may be stored in the smart device and/or transmitted to the physician of the user. It is however to be understood, as mentioned above, that the information, written and/or visual and/or audible, may be comprised in the programs or the applications that may be stored in the smart device. The user may also be alerted by the smart device of any deviations and may possibly be given options regarding remedy of the deviations.

As an alternative to NFC-technology, other types of short-range wireless technology (SRWT) may be utilized for obtaining the same functionality. There are a number of different short-range technologies that may be used, where ANT+, RFID, Zigbee and Bluetooth are the technologies that are the best suited for implementation in medicament delivery devices. One favourable technology is then the Bluetooth-technology. Bluetooth technology operates in the unlicensed industrial, scientific and medical (ISM) band at 2.4 to 2.485 GHz, using a spread spectrum, frequency hopping, full-duplex signal at a nominal rate of 1600 hops/sec. The 2.4 GHz ISM band is available and unlicensed in most countries. Especially the Bluetooth low energy or Bluetooth Smart may be utilized in connection with medicament delivery devices and the functions that are requested. The Bluetooth circuit is provided with a transmitter that is capable of transmitting for instance a unique identification number or data as well as recording a time stamp. The Bluetooth circuit is driven by a small battery, wherein some sort of switch preferably is arranged between the battery and the Bluetooth circuit for activating the Bluetooth circuit only when there is an occurrence or change of status of the medicament delivery device.

One scenario regarding the present invention is to provide more information regarding the status of the medicament delivery device in the communication between one or more SRWT-chips and smart devices, thereby increasing the level of integration between the medicament delivery device and the smart device. An example of this is shown in FIG. 2. In this scenario, SRWT-chips are used that are capable of detecting and identifying if a certain circuit on the medicament delivery device is open or closed. This capability may be used for providing information regarding the status of the medicament delivery device.

Figure 6:
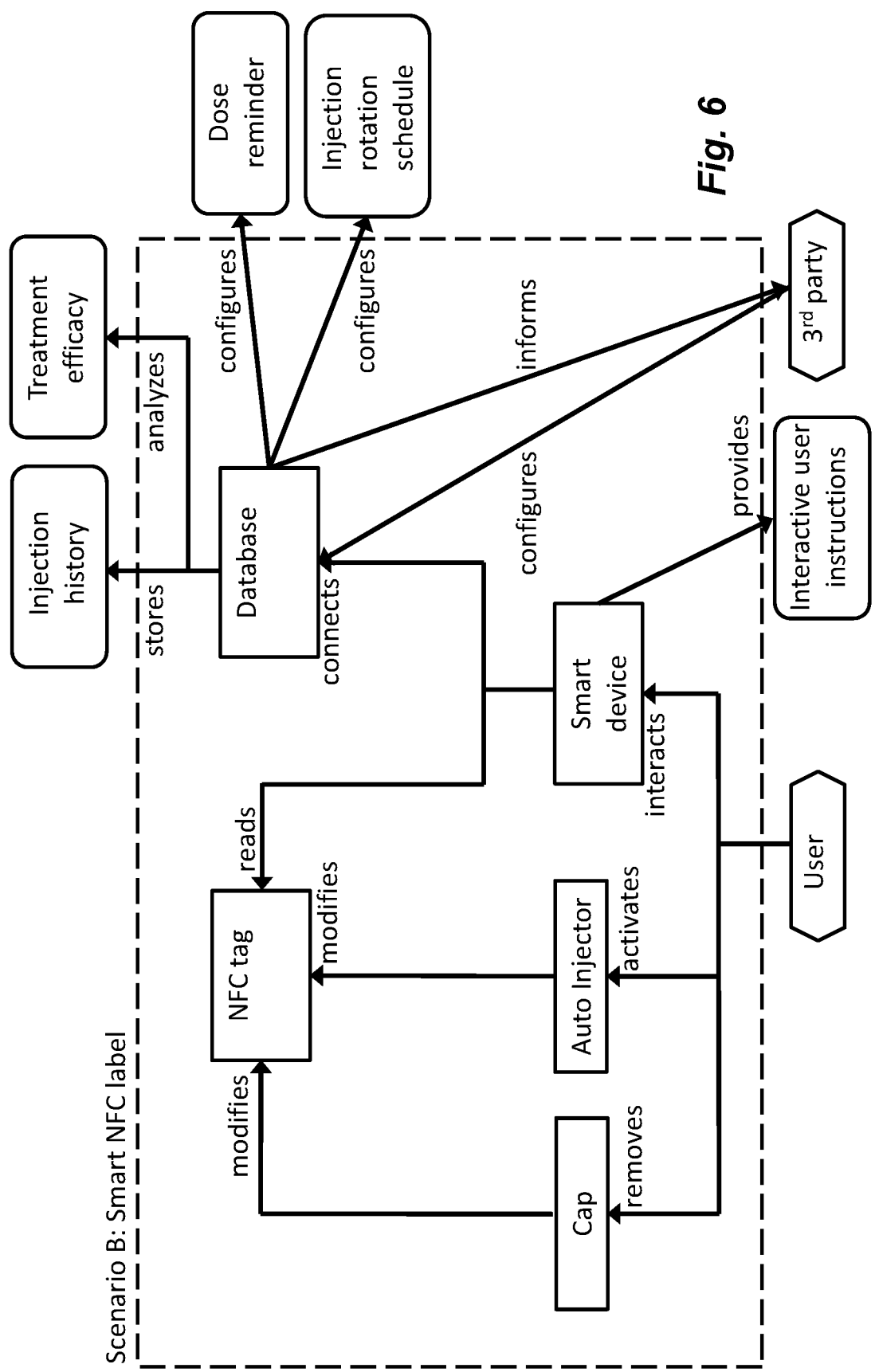

For instance circuits may be connected to a number of functions and components of the device. One important function is as an information provider. As an example, a circuit 40 such as an NFC-circuit, may be arranged as a label that is attached to an outer surface of a medicament delivery device. As seen in FIGS. 2A and 2B, one part of the label may be the electronics circuit with an antenna capable to transmitting information to an external receiver such as a smart device. As seen in FIGS. 2A and 2B, the electronics circuit may be arranged in the label having an activation element 42 in the form of an electrical circuit element extending over the interface between a housing 43 of the medicament delivery device and a protective cap 44. Further the label may be arranged with a tear line 46 that is generally aligned with the interface between the housing and the protective cap. When a user removes the protective cap 44 the circuit is broken and thus closed, which may be detected by the NFC 40 and this information may be transmitted to the smart device as seen in FIG. 6. The smart device can store this information and/or transmit it to external databases, adding to the device history, which may be monitored by e.g. the physician of the user.

FIGS. 3 to 5 show a similar scenario, but in this case, a label 50 is only arranged between the protective cap 44 and the housing 43 of a medicament delivery device. Further, the label is arranged with a Bluetooth chip 52, FIG. 4, with an antenna 54 as well as a small battery 56. The Bluetooth chip is arranged with a micro controller unit and memory storage elements, which storage elements may comprise handling instructions for the micro controller unit as well as unique identification information. An activation element 58 in the form of an electrical circuit element is designed in the label, extending over a tear line 60 that generally follows the interface between the protective cap 44 and the housing 43. When the medicament delivery device is to be used, the protective cap 44 is removed. This will cause the label 50 to be torn along the tear line 60, which will cause the activation element 58 to be affected such that the battery 56 will power up the Bluetooth chip.

The activation of the battery and the Bluetooth circuit may be performed in several ways. For instance, as seen in FIG. 5, the tearing of the label 50 may cause a strip 62 of non-conductive material placed against one terminal of the battery 56 to be removed, thereby closing a circuit. On the other hand, the Bluetooth circuit may be connected to the battery but being in stand-by mode and in intervals checking if a circuit has been broken. If so, the Bluetooth will switch into active mode. The Bluetooth chip will then start to send signals to possible receivers. In this aspect it is to be understood that the receiver may be the smart device of the user only so that information from the medicament delivery device cannot be transmitted to other Bluetooth receivers.

The data transmitted may be a unique identification number enabling the identification of the unique medicament delivery device. Together with this information should be a time stamp for determining when the medicament delivery device has been activated for providing a dose of medicament. Further, the label may be arranged with information providing the possibility of obtaining the unique identification number when the Bluetooth chip is not activated. The information transmitted by the Bluetooth circuit may on the one hand be used for indicating the use of the medicament delivery device, and on the other hand be used for tamper evidence of the medicament delivery device.

Regarding the unique identification number that the Bluetooth circuit may transmit, it may in addition be arranged on the surface of the label 50 in the form of e.g. machine readable indicia, such as a QR-code 62 as shown in FIG. 3. The advantage with this is that it is possible to identify the specific medicament delivery device without having to activate the Bluetooth circuit. This is an advantage when the medicament delivery device is handled after manufacturing, such as by a pharmacist that is to provide a user with medicament delivery devices according to treatment schemes. It is then easy to read the unique codes of specific medicament delivery devices and to assign them to specific users.

Circuits may be connected to a number of components for providing status information. Such status information may comprise end of dose delivery. It may for example be important for a user to know when an injection sequence has ended and that it is safe to remove the device from the injection site. In this case a circuit may be affected by moving components at the end of dose delivery, wherein the circuit acts as a switch, e.g. from open to closed, FIG. 3. The switch information detected by the SRWT is transmitted to the smart device, wherein the smart device is arranged to indicate to the user that the device may safely be removed. Also, this information confirms that the device is used.

The circuits and switches may further be used as interactive, step by step, instructions. For example, the smart device may be provided with an instruction application showing a user in a step-wise manner how a device should be handled. When one step has been performed, whereby a certain circuit has been affected and detected by the SRWT and transmitted to the smart device, an OK or positive response is provided by the smart device and displayed to the user. The instruction application then shows the subsequent handling step to be taken. In this manner, all steps affect different circuits that in turn provide the SRWT-chip with status information. This status information is successively transmitted to the smart device and appropriate information is displayed to the user by the instruction application.

In connection with the increased integration of the medicament delivery device and the smart device, further information could be collected in order to increase the understanding of the effects of a certain treatment scheme, e.g. disease monitoring. The programs or applications that are used in the smart device in connection with the medicament delivery devices may further include questionnaires that are filled in by the user in connection with a dose delivery operation. The questionnaire may include a number of questions regarding the current status of the patient and may preferably be configurable depending on therapy, disease and user needs. The areas that might be handled may include quality of life, cognitive function, pain, fatigue, nausea, mental health, etc. The answers of the questionnaire may then be transmitted from the smart device to external databases together with information collected via the SWRT-tags for processing and evaluation to find positive or negative correlations between the treatment scheme and type of medicament in relation to the perceived condition of the patient.

Figure 7A:
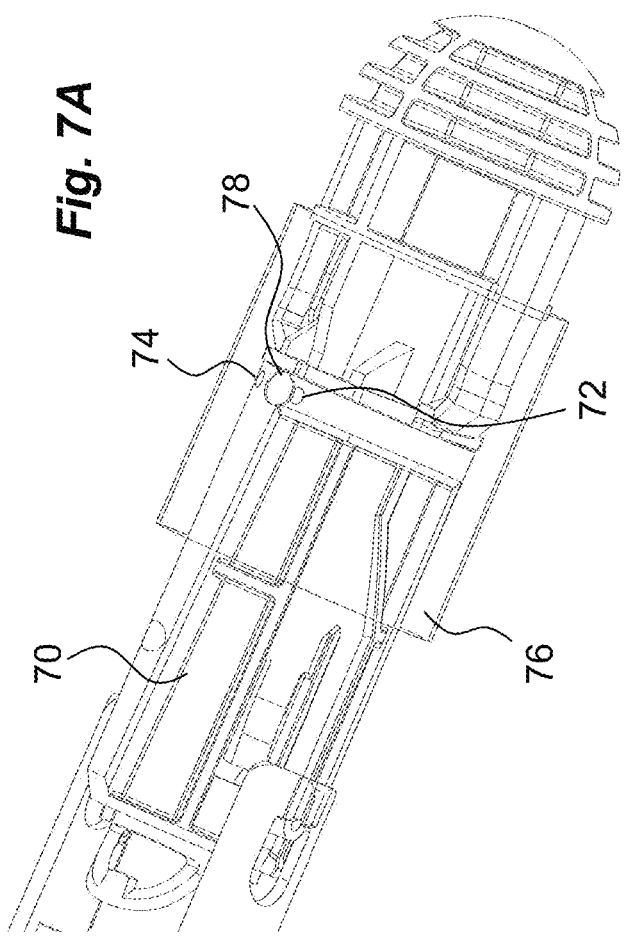
Figure 7B:
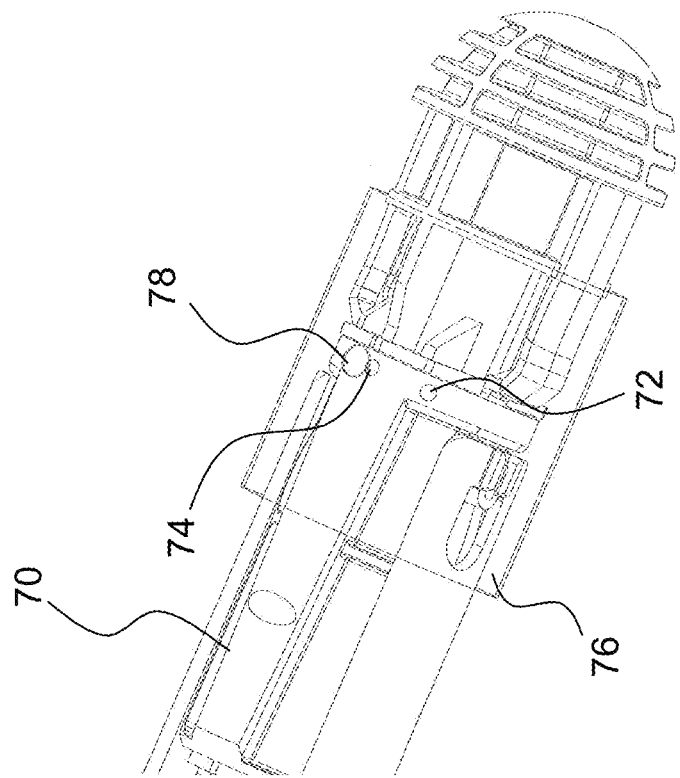

It is to be understood that more than one SWRT-circuit may be used on one device, where the different SWRT-chips are arranged to handle for example different states of a device. In this scenario, when e.g. NFC-tags are used, it may be important that only one NFC-tag at the time may be read by the smart device. FIGS. 7a and 7B show a possible use of several NFC-tags. Here the medicament delivery device is arranged with a component 70 that is rotatable inside the housing of the device. Before dose delivery the component 70 has one rotational position, FIG. 7A, and after completed dose delivery, the component 70 has a second rotational position, FIG. 7B. This fact may be used in that each position provides information from separate NFC-tags 72, 74. In order to ascertain that only one NFC-tag at the time can be read, a metallic layer 76 is attached to the housing of the medicament delivery device in the area of the NFC-tags, where the metallic layer 76 acts as a shield, blocking reading of the NFC-tags. The metallic layer 76 is further arranged with an opening 78, which opening 78 is positioned in relation to the NFC-tags 72, 74 such that a first NFC-tag 72 is aligned with the opening 78 at the first position of the rotatable component, FIG. 7A, and that a second NFC-tag 74 is aligned with the opening 78 in the second position, FIG. 7B.

Thus, in the first position, before being used, the first NFC-tag 72 may be read by a smart device, providing information that the device is unused. Further, in the second position, after use, the second NFC-tag 74 may be read by a smart device, providing information that the device has been used. It is to be understood that further NFC-tags may be used, for instance as described above in connection with removal of a protective cap. There are numerous ways in which the functions may be physically implemented. For instance, the several NFC-tags may be integrated into the material when the rotatable component is manufactured, e.g. moulded in plastic. The NFC-tags may also be attached onto the surface of the rotatable component, either glued directly or being integrated in a label that is attached to the rotatable component. Also the metallic layer may be formed in different ways. It may also be integrated in the material of the housing or be arranged as a label that is attached on the inner or outer surface of the housing.

According to a further scenario of the present invention, an attachment 80 could be provided to the smart device, FIG. 5. The attachment could for example comprise a shell enclosing at least part of the smart device. This attachment enables a number of features and functions.

Preferably the attachment is arranged to accommodate or hold a medicament delivery device. It is even feasible that the attachment and the medicament delivery device are integrated into one unit. With this feature, an even closer integration between the medicament delivery device and the smart device is obtained. This in turn provides additional advantages and features. One advantage is that the fixed connection between the medicament delivery device and the smart device enables correct reading position of a SRWT-tag and in particular an NFC-tag having a short range. Thus, the user does not have to try different distances between the medicament delivery device and the smart device in order to obtain information from the NFC-tag.

Further, if the smart device is not equipped with an NFC-reader, the attachment could be provided with such an NFC-reader, thereby adding functionality to the smart device. The integration of the medicament delivery device and the smart device further provides real time interactive user instructions as well as correct injection times, dates and dose quantities because of the close connection between the medicament delivery device and the smart device because of real time reading of the NFC-tag. The injection times, dates and dose quantities can be recorded directly in the smart device for further processing or transmittal.

Many smart devices are arranged with motion sensors in three dimensions, which functionality could be used in connection with handling of the medicament delivery device. For instance, the smart device could detect how it, and thus the medicament delivery device, is being held. This may be important for some types of drugs and for some types of medicament delivery devices in that the medicament delivery device has to be held in a certain way during some steps when used. This could for example be a medicament delivery device using a so called dual chamber medicament container, where it can be important how the medicament container is held during mixing and priming. The motion sensors of the smart device could then be used to detect how the medicament delivery device is held and could inform a user on how to hold the device and alert the user if the device is not held according to instructions.

Further features of the smart device that could be used with the integrated medicament delivery device include the use of a camera that is often an integrated part of the smart device. The camera could then be used to take photographs of the content of the medicament container, which often is transparent, in order to obtain information regarding the status of the drug. For example, colouring or opacity of a drug may indicate that something adverse has happened to the drug, such as exposure to temperatures outside the prescribed range, such that the drug should not be used. The comparison of colour or opacity may be performed directly by the user in an application in the smart device, or the picture may be sent by the smart device to an external site where skilled personnel perform the comparison and alert the patient of any deficiencies of the drug and advice as to how proceed.

Regarding adherence and patient responsibility, there are features and functions of the smart device that may be utilized. Some drugs and treatment schemes are very expensive to the national healthcare authorities and a lot of responsibility is put on the users to really adhere to the treatment schemes. There has been discussions in several countries in the world that if patients do not adhere to an expensive treatment, they should be forced to pay for the continued treatment, fully or partly, the arguments being that those persons that are not interested enough in a treatment should have to pay for it. The information and drug delivery history obtained from the NFC-tags could be used to monitor the adherence.

In that respect, biometrical sensors such as fingerprint sensors, eye and/or face recognition via cameras on the smart devices mat provide proof of a user of a certain medicament delivery device, providing proof that it is the legitimate user that has activated the medicament delivery device for delivering a dose. Biometrical sensors may further be used in order to ascertain that the device cannot be accidentally, or willfully, used by a third person.

The functionality of the NFC-tags may be further enhanced by adding a battery in that a timestamp of activation is achievable. For instance, when a switch as described above is affected, such as closing a circuit, a power circuit from the battery is activated. An internal clock in the NFC-chip is thereby activated, starting to count elapsed time. This time information is then transmitted to the smart device, which could be used for a number of functions. For instance, if the clock is activated by an end of dose delivery sequence, then the smart device can easily calculate when a subsequent dose delivery is due according to dose delivery schemes contained in e.g. applications in the smart device. The smart device could then generate reminders to a user until the smart device has read information from another NFC-tag that a subsequent dose has been delivered.

Additional functionality when using a battery is that correct time information of a performed function of the medicament delivery device, such as dose delivery, is obtained regardless of when the information is read from the NFC-tag. Further, when monitoring users of a medicament delivery device during clinical trials, the feature could be used as a hidden stamp of e.g. injected dose. Used devices are then collected by the organiser of the clinical tests and actual times as read from the NFC-tags are compared with the times stated by the users in their handling notes.

One type of battery that could be used is a small one, such as a thin printed battery or a small button cell. For the above purposes there is a low capacity requirement since the battery is activated only when needed and is only used for powering the internal clock, thus there is no standby consumption. However, it is of course possible to use larger batteries in connection with NFC-tags, which enables further features and functions.

For example, if a larger battery is used, the NFC-tag could use the temperature sensor that is built into the NFC-chip. This may be an advantage because then the temperature of a medicament delivery device and/or a medicament container may be monitored and logged for instance during transport. This might be important for a number of drugs that are temperature sensitive, whereby it can be ensured that the quality of the drug has not been affected by temperature variations outside approved ranges. Also, the temperature sensor could be used to provide information when a drug has reached a target temperature for delivery. The information is then communicated to the smart device, where the latter provides handling and temperature information to the user.

When a larger battery is used, the NFC-tag could be arranged with LED's of different colour, or one LED that can change colour. The LED's are then connected to the NFC-tag such that when the temperature sensor senses a certain temperature, a certain colour is lit. When the temperature changes above or below a threshold, another colour is lit. For example, if the temperature of a drug is above or below a permissible drug delivery temperature range, then one colour is lit, e.g. a red light, indicating that the drug cannot be used yet. When then the temperature reaches the permissible range, e.g. room temperature, then the light is changed to e.g. green, indicating that the drug now may be used.

Furthermore, the temperature sensor of the NFC-chip may be used to indicate when medicament container has been emptied, i.e. a dose delivery has ended. If the NFC-tag is placed properly in relation to the medicament container, the temperature sensor may sense the temperature change that occurs between the temperature of the drug and the temperature of the empty medicament container. This significant temperature change may be used to trigger information to the smart device that the dose delivery had ended and that it is safe to remove the device. Also here, when a larger battery is arranged, there is enough power to drive for instance a light source, a vibrator and/or a summer connected to the NFC-circuit, in order to provide visual, tactile and/or audible information that a dose has been delivered.

Figure 8:
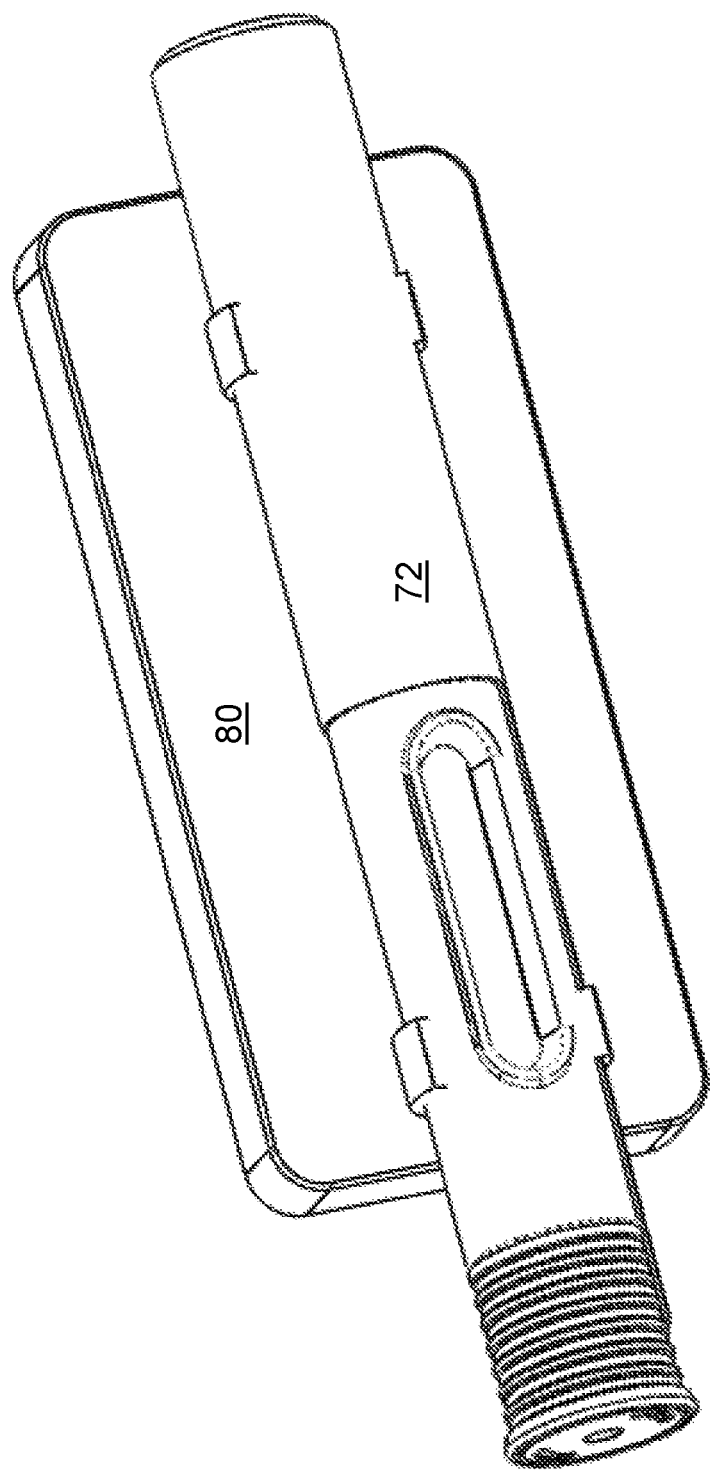
Figure 9:
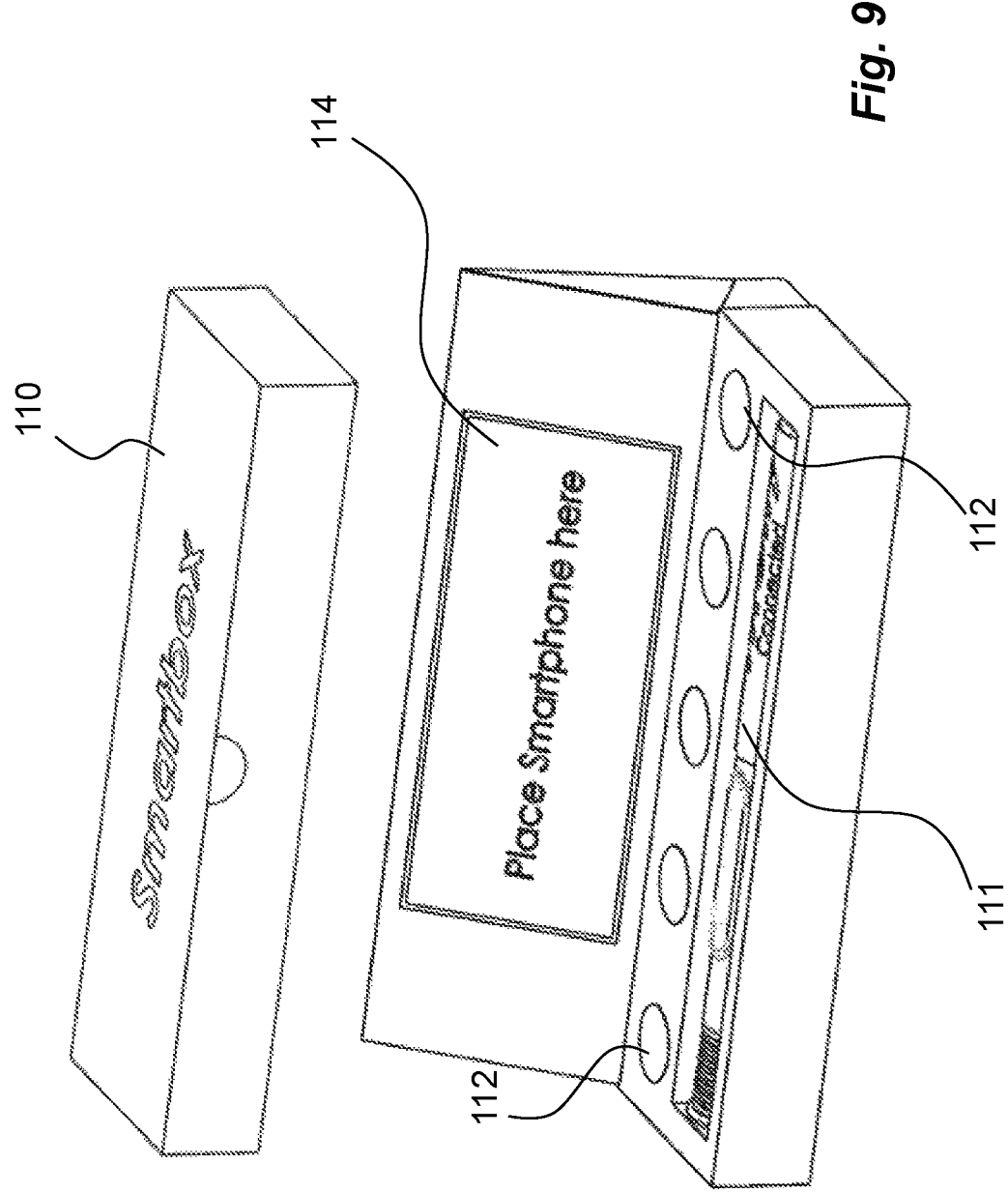
Figure 10:
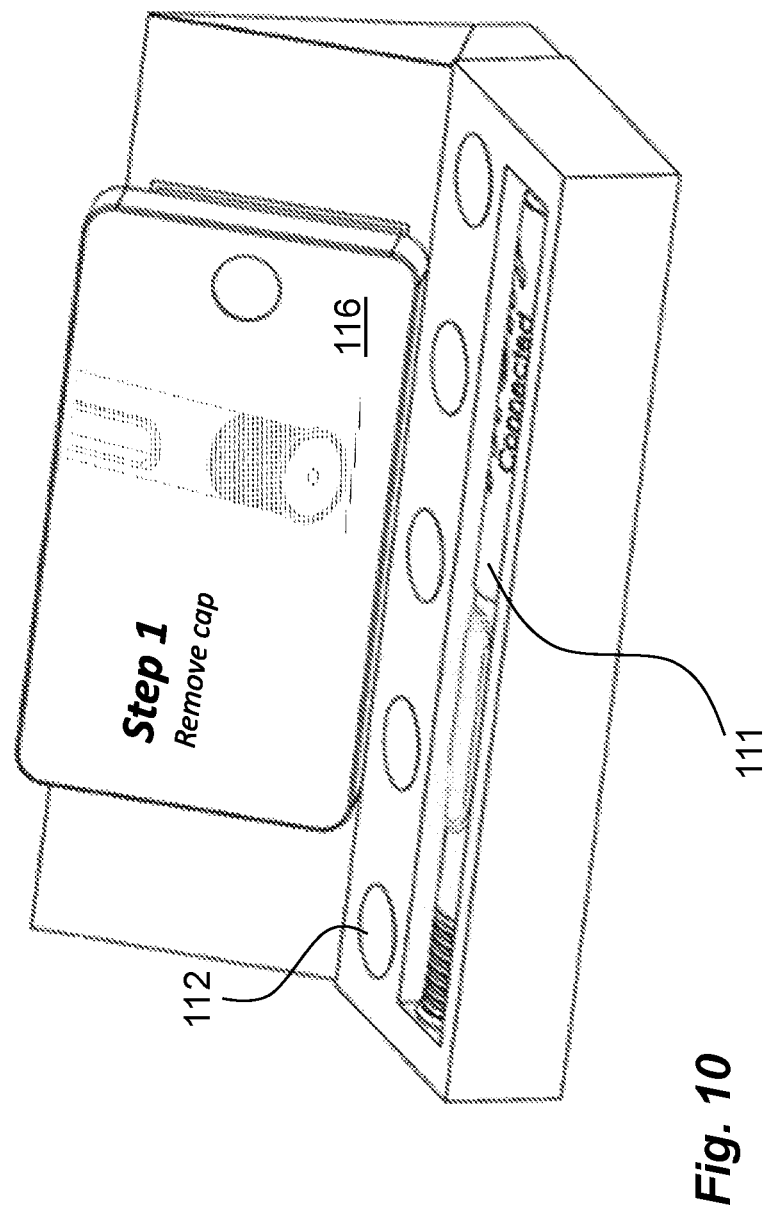

There are further areas where SRWT-tags could be used together with smart devices in medicament delivery device applications. For tutorial purposes, for instance for first time users, a packaging 110 of a medicament delivery device 111 may be used for tutorial purposes as well as for installing specific programs and applications in a smart device, which programs and applications are to be used together with the medicament delivery device, FIGS. 8 and 9.

In this context, the packaging 110 of the medicament delivery device may be arranged with for example an NFC-chip and suitable circuitry. The NFC-chip and the circuitry are preferably embedded in the packaging 110. A number of printed button areas 112 may be provided on the packaging, under which the circuitry is placed so that pressing on the printed button areas 112 will affect the circuitry so as to activate the NFC-chip to provide certain information. The packaging 110 may further comprise a marking 114 where to place a smart device 116, FIG. 9, wherein the marking 114 of the position of the smart device 116 is chosen such in relation to the NFC-antenna that a good connection is obtained. When a smart device 116 is placed on the marking 114 of the packaging, the NFC-chip is energized by the smart device 116. This could in turn cause an application to be installed in the smart device 116 and started. Then, depending on which button 112 is pressed on the packaging 110, different information is provided through the smart device. The information could for example include instructions for use that could be step by step and displayed sequentially when pressing the buttons 112.

In addition to the medicament delivery devices described above, there might be further devices available to a user, or further functional features of the medicament delivery device, that could add to the functionality. For instance, additional sensors may be employed for measuring hard facts regarding the patient, where the information from the additional sensors are added to the patient history both regarding dose delivery adherence as well as health reports as established by questionnaires as mentioned above. The hard facts measured may come from blood samples, monitored heart rate, blood pressure measurements, saliva samples, just to mention a few.

It is to be understood that the embodiments described above and shown in the drawings are to be regarded only as non-limiting examples of the invention and that it may be modified in many ways within the scope of the patent protection.

The invention claimed is:

1. A medicament delivery device comprising:
   a housing configured to receive a medicament container containing a medicament;
   a delivery nozzle that is configured to deliver the medicament into a user;
   a protective cap that is removably arranged on the housing;
   a breakable information tag that comprises an antenna, where the breakable information tag is arranged both on a portion of the housing and on a portion of the protective cap,
   wherein the breakable information tag is configured to be broken upon the removal of the protective cap from the housing,
   wherein the breakable information tag is configured with first electronic readable information and second electronic readable information, and
   wherein the second electronic readable information can only be read by a smart device when the breakable information tag is broken.

2. The medicament delivery device according to claim 1, wherein the first electronic readable information includes information related to the medicament or to the user.

3. The medicament delivery device according to claim 1, wherein the first and second electronic readable information are read by the smart device.

4. The medicament delivery device according to claim 3, wherein the first and second electronic readable information start an information providing program in the smart device.

5. The medicament delivery device according to claim 1, where the breakable information tag further comprises an activation element.

6. The medicament delivery device according to claim 5, where the activation element is triggered when the protective cap is removed from the housing, where the activation element causes energization of a short-range wireless communication device incorporated in the breakable information tag.

7. The medicament delivery device according to claim 1, where the breakable information tag further comprises a battery that is activated when the protective cap is removed from the housing.

8. The medicament delivery device according to claim 1, wherein the breakable information tag further comprises a temperature sensor.

9. The medicament delivery device according to claim 1, where the second electronic readable information comprises an NFC-tag.

10. The medicament delivery device according to claim 9, where the NFC-tag is shielded and non-readable prior to the protective cap being removed.

11. The medicament delivery device according to claim 10, where breaking the breakable information tag un-shields the NFC-tag such that the smart device can read the NFC-tag.

12. The medicament delivery device according to claim 1, where the breakable information tag further comprises an NFC circuit, wherein breaking the breakable information tag breaks the NFC circuit, where the break is detected by the NFC circuit and causes the second electronic readable information to be transmitted to the smart device.

13. A system comprises:
    a smart device comprising a processor, a storage, a communication system; and
    a medicament delivery device comprising:
    a housing configured to receive a medicament container containing a medicament;
    a delivery nozzle that is configured to deliver the medicament into a user;
    a protective cap that is removably arranged on the housing;
    a breakable information tag that comprises an antenna and an activation element, where the breakable information tag is arranged both on a portion of the housing and on a portion of the protective cap,
    wherein the breakable information tag is configured to be broken upon the removal of the protective cap from the housing,
    wherein the breakable information tag is configured with first electronic readable information and second electronic readable information,
    wherein the smart device is configured to read the first electronic readable information or the second electronic readable information, and
    wherein the activation element is triggered when the protective cap is removed from the housing such that the second electronic readable information can then be read by the smart device.

* * * * *